United States Patent [19]

Draenert

[11] Patent Number: 5,728,160
[45] Date of Patent: Mar. 17, 1998

[54] MEMBRANE SEAL FOR SEALING APERTURES IN BONES

[76] Inventor: Klaus Draenert, Gabriel-Max-Str. 3, D-81545, Muchen, Germany

[21] Appl. No.: 807,211

[22] Filed: Feb. 28, 1997

Related U.S. Application Data

[63] Continuation of Ser. No. 583,665, Jan. 5, 1996, abandoned, which is a continuation of Ser. No. 356,238, filed as PCT/EP93/01511 Jun. 15, 1993 published as WO93/25163 Dec. 23, 1993, abandoned.

[30] Foreign Application Priority Data

Jun. 15, 1992 [DE] Germany .............. 42 19 564.0

[51] Int. Cl.$^6$ .............................................. A61F 2/28
[52] U.S. Cl. .............................. 623/16; 623/23; 606/92; 606/94
[58] Field of Search .................... 623/16, 18, 23, 623/33, 35; 602/63, 74; 606/86, 92, 93, 94, 140, 141, 201, 202, 203; 128/844, 918

[56] References Cited

U.S. PATENT DOCUMENTS

| | | | |
|---|---|---|---|
| 2,636,492 | 4/1953 | Wright | 602/63 |
| 2,834,025 | 5/1958 | Leavy | 623/33 |
| 4,186,448 | 2/1980 | Brekke | 623/16 |
| 4,488,549 | 12/1984 | Lee et al. | 606/94 |
| 4,562,598 | 1/1986 | Kranz | 606/92 |
| 4,822,368 | 4/1989 | Collier | 623/22 |
| 4,848,324 | 7/1989 | Gavriely | 602/63 |
| 4,888,024 | 12/1989 | Powlan | 623/23 |
| 4,997,448 | 3/1991 | Filer | 623/23 |
| 5,047,030 | 9/1991 | Draenert | 606/65 |
| 5,047,061 | 9/1991 | Brown | 623/23 |
| 5,147,366 | 9/1992 | Arroyo et al. | 606/94 |
| 5,195,537 | 3/1993 | Tillotson | 128/844 |
| 5,284,159 | 2/1994 | Wilk | 128/844 |
| 5,507,749 | 4/1996 | Draenert | 606/94 |

FOREIGN PATENT DOCUMENTS

| | | |
|---|---|---|
| 0 073 604 | 3/1983 | European Pat. Off. . |
| 0 093 560 | 11/1983 | European Pat. Off. . |
| 0 315 283 | 4/1989 | European Pat. Off. . |
| WO 90/00375 | 1/1990 | WIPO . |

*Primary Examiner*—Michael J. Milano
*Attorney, Agent, or Firm*—Westman, Champlin & Kelly, P.A.

[57] ABSTRACT

The present invention relates to a device for sealing an opened tubular bone, a bone foramen, an osteotomy surface, a bone fenestra or a fracture line. The present invention proposes an elastic membrane (10) which is positioned over the end of a bone and/or pressed against the bone, such that a vacuum can advantageously be generated within the bone.

9 Claims, 3 Drawing Sheets

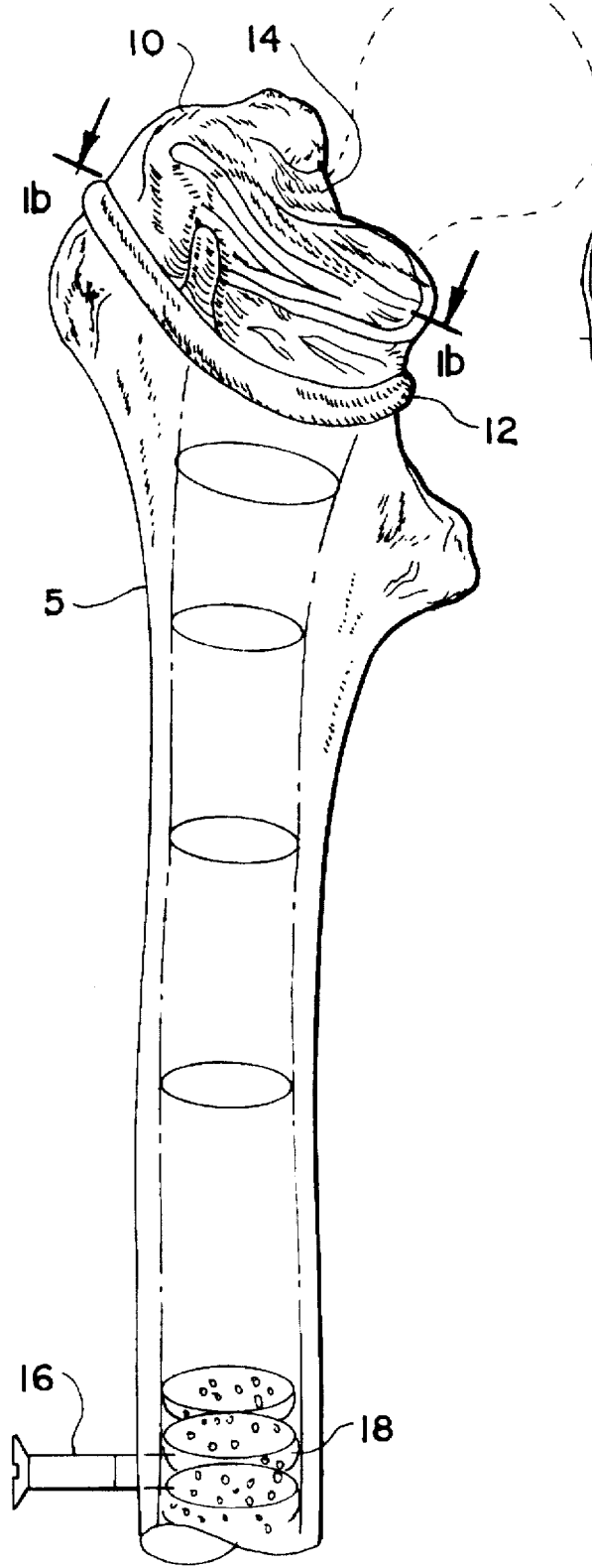
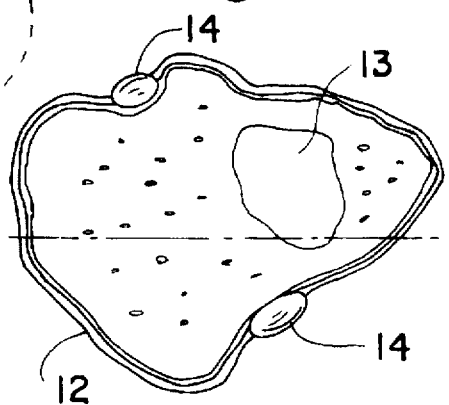
Fig. 1a
Fig. 1b

U.S. Patent    Mar. 17, 1998    Sheet 3 of 3    5,728,160
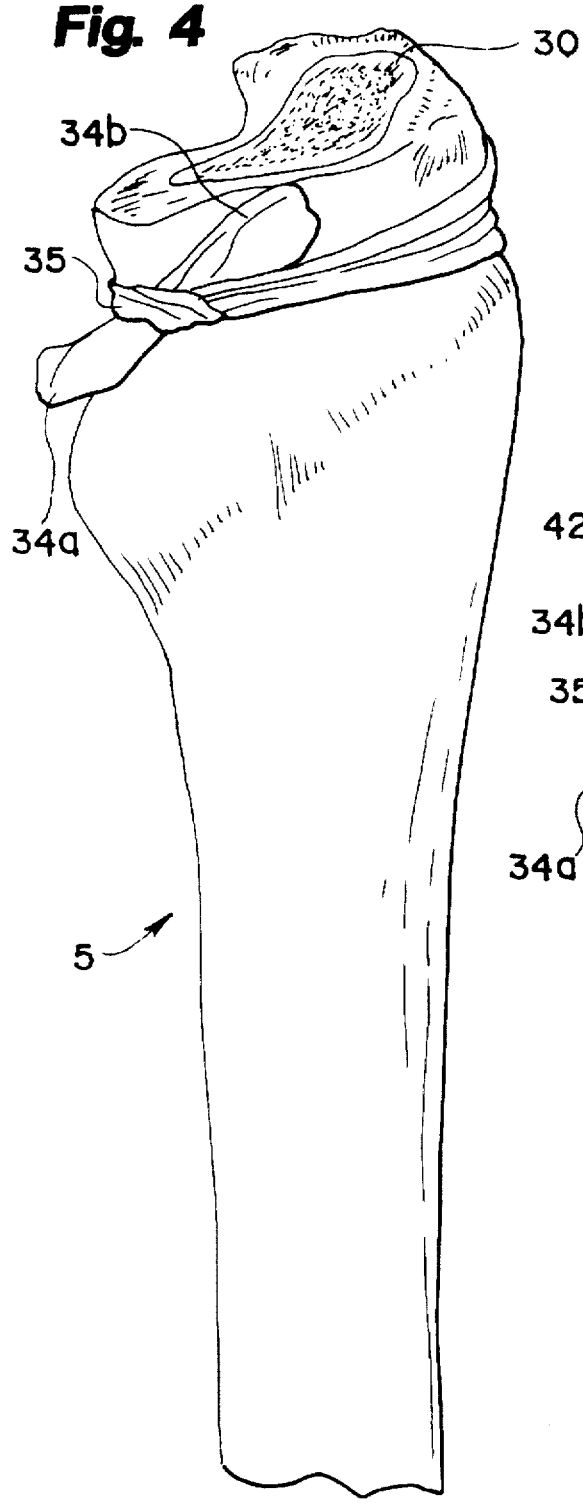
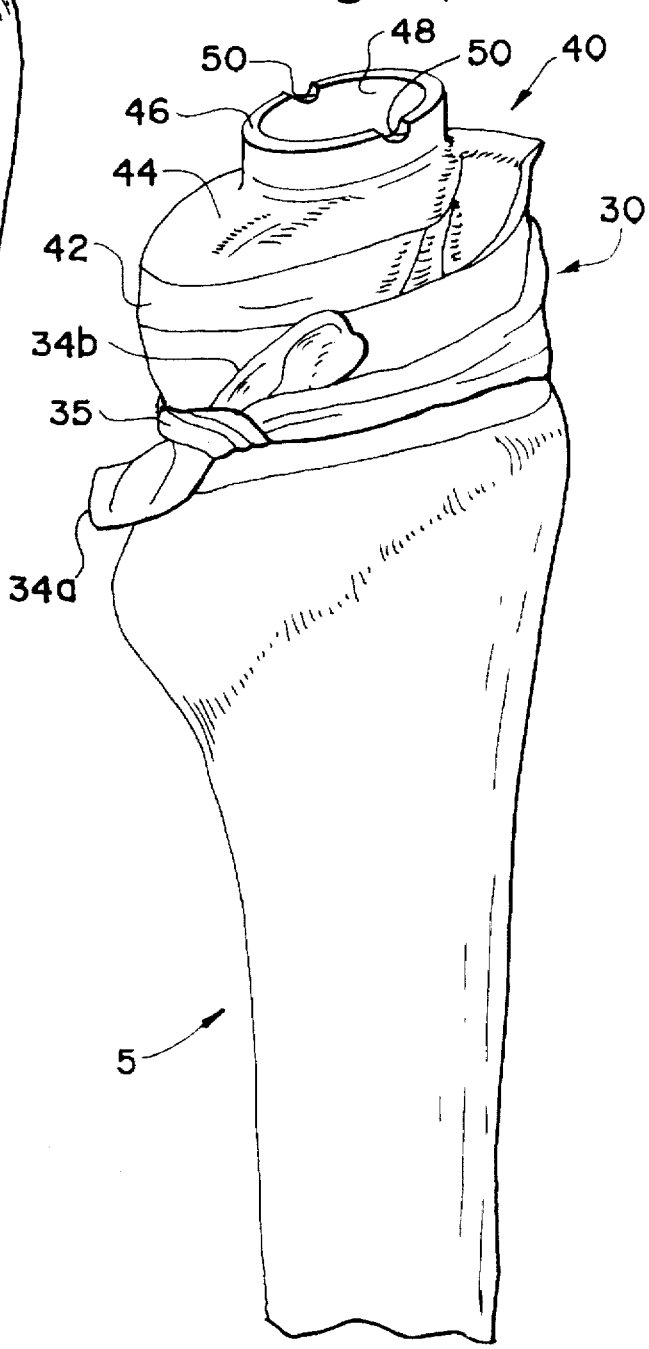

MEMBRANE SEAL FOR SEALING APERTURES IN BONES

CROSS REFERENCE TO RELATED APPLICATIONS

This is a continuation of application Ser. No. 08/583,665, filed on Jan. 5, 1996, which was a continuation of application Ser. No. 08/356,238, filed as PCT/EP93/01511 Jun. 15, 1993, published as WO93/25163 Dec. 23, 1993, both now abandoned

BACKGROUND OF THE INVENTION

The present invention relates to a device for sealing an opened tubular bone, a bone foramen, an osteotomy surface, a bone fenestra or a fracture line. In particular, the present invention concerns a membrane seal for sealing apertures in bones.

From WO 90/00375, and its equivalent U.S. Pat. No. 5,507,749, a device for sealing the medullary cavity of a bone when applying bone cement is known, which comprises an elastic bottom portion for achieving a positive contact with the bone around the medullary cavity and a rigid top portion for pressing the elastic bottom portion against the bone. This device is particularly advantageous if the elastic bottom portion can be pressed via a bone cement cartridge against an essentially even surface, such as a resection plane.

In U.S. Pat. No. 4,997,448, a seal is described which is directly inserted in the proximal femur and pressed against the wall of the bone during insertion of a stem of a prosthesis, thus providing a cement pressurization when the stem is pushed into the medullary cavity. There is, however, no seal described which enables sealing an opened bone by covering it in a vacuum tight member without obstructing the cancellous bone structure.

It is an object of the present invention to provide a device for sealing apertures in bones, which is versatile and in particular seals uneven bone surfaces as well.

This object is achieved by the device according to the invention.

SUMMARY OF THE INVENTION

The present invention is based on the idea of providing an elastic membrane which can be arranged around the bone aperture so as to seal the bone such that a vacuum can be generated within the bone. For this purpose, the elastic membrane can for example be positioned over the end of the bone and/or pressed against the bone.

Preferably, the membrane according to the invention has the shape of a hollow cylinder which is open at one end, a finger stall, a cap or a cup. If not stretched, the membrane can also be plain and approximately circular or ellipsoidal or oval. The free edge of the membrane can be compressed or thickened. Such a finger stall can simply be positioned over the end of the bone in a sealing manner or pressed against the bone. A membrane consisting of silicone is advantageous.

The elastic membrane can preferably have thickenings for sealing contours, indentations, pits and/or apertures (foramina).

Moreover, the elastic membrane can be provided with predetermined rupture sites, predetermined perforations and/or openings.

At the free edge of the elastic membrane, means can be provided by means of which the membrane can sealingly engage with the bone. A guided or fixed elastic or tensile pulling device can for example be provided at the free edge of the membrane. For this purpose, the membrane can also be provided with tags which can be knotted around the circumference of the bone so as to seal it.

It is particularly advantageous if a tubular cavity is provided at the free edge of the membrane. This cavity can for example be inflated by means of gas or a fluid and then forms a kind of seal which can be sealingly arranged around the bone aperture.

It is also possible to provide several different, graded sizes of the membrane according to the invention, in particular of the finger-shaped device according to the invention, in order to provide a variety or set for sealing bone apertures of different sizes and shapes.

BRIEF DESCRIPTION OF THE DRAWINGS

FIG. 1 shows the device according to the invention in the form of a membrane seal for sealing the proximal end of a femur;

FIGS. 3 and 4 show an embodiment of the device according to the invention in the form of a finger stall which is provided with tags; and FIG. 5 shows a device according to the invention in combination with an additional device for sealing the medullary cavity for use when applying bone cement.

DETAILED DESCRIPTION OF THE PREFERRED EMBODIMENTS

Figure 2:
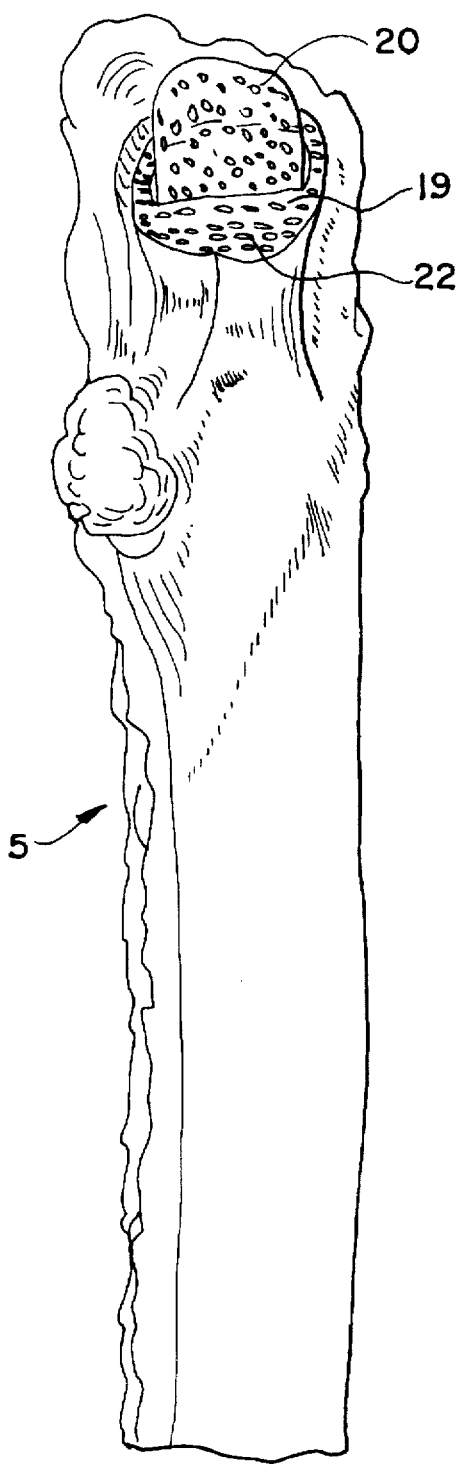
FIG. 2 shows a femur opened for the application of bone cement.

FIG. 1a shows the proximal end of a femur 5 in anterior posterior projection being provided with a sealing device 10 according to the invention in the form of an elastic membrane preferably made of silicone overlying and sealing the proximal end of the medullary cavity 19. A cannulated screw 16 passes into the femur and opens to the medullary cavity at a location remote from the open proximal end. A plug 18 anchors the inner end of the cannulated screw 16 inside the medullary cavity. The screw 16 is used for providing a vacuum to the upper portion of the cavity when the proximal end is sealed.

The sealing device 10 is positioned over the opened proximal end of the femur approximately like a cap and its free edge is provided with an inflatable bulge or bead 12. The bulge 12 forms a seal at the free end of the elastic membrane of the sealing device 10 such that upon positioning the device 10 over the free end of the bone at least a partial vacuum can be generated within the bone by applying vacuum through screw 16. Moreover, approximately in the middle of the sealing device 10 two further bulges or thickenings 14 of the elastic membrane are provided which are formed at the front and the backside of the edge of the membrane forming the seal and contact and are seated in the intertrochanteric fossa at the right and the left side, respectively. For generating a vacuum in the inside of the bone. The cannulated suction drainage screw 16 is used for generating a vacuum inside the bone. The screw is, for example, described in EP-A-305 417 and its corresponding U.S. Pat. No. 5,047,030, and is anchored in plug 18. FIG. 1b shows a cross-section of along the line A—A FIG. 1a, in which the two bulges or thickenings 14 are shown at the circumferential bulge 12. Reference sign 19 designates the aperture of the medullary cavity.

FIG. 2 shows the medial view of an opened femur which can be sealed by means of the sealing member made according to the invention. Reference sign 20, designates a lateral section of an upper end of the vertical wall at the femoral neck in which the circles signify openings that will take up applied bone cement. Reference sign 22 indicated the top of the femur wall as shown by a section through the neck of the femur. The section, as can be seen, is inclined relative to the axis of the femur, and the top of the bone surrounds the medullary cavity 19. This sectioned wall forms a "U" shape around the cavity 19 at the femoral neck which joins the upper end of the vertical wall portion shown at 20.

Figure 3:
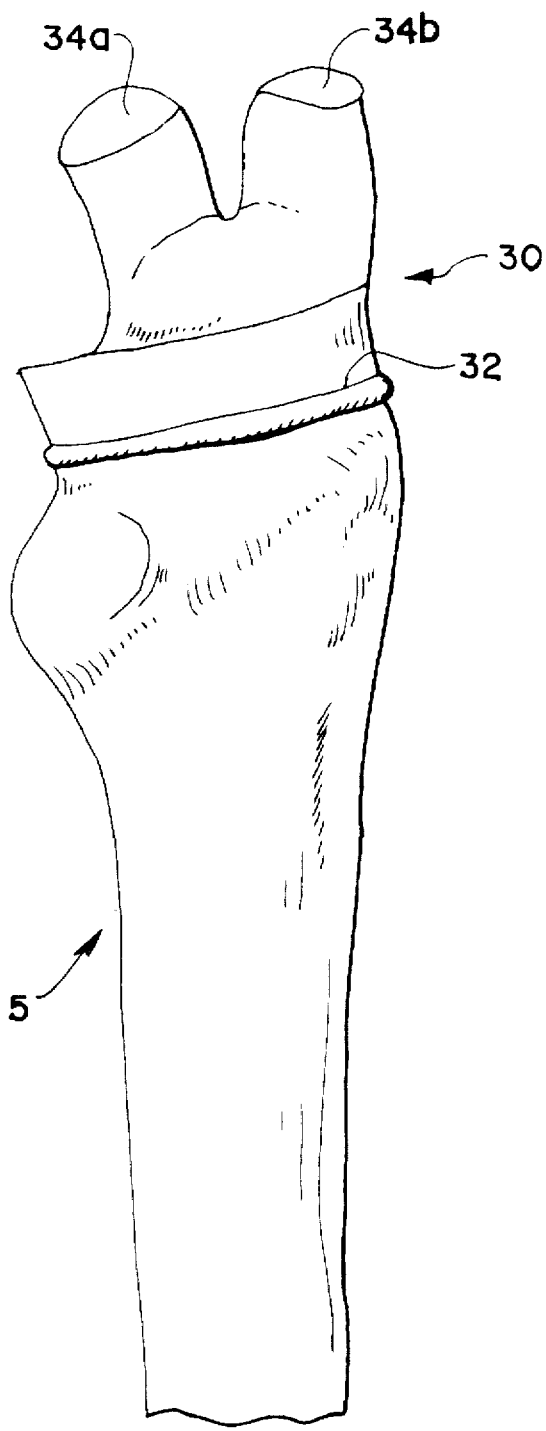

FIG. 3 is a ventromedial view of the femur which is turned by about 30° with respect to FIG. 2. On the femur 5, a sealing device 30 according to the invention in the form of a finger stall having a circumferential bulge 32 and two tags 34a and 34b which, as shown, are short cylinders formed by the finger stall. The finger stall is positioned over the opened proximal end of the femur.

FIG. 4 shows the next step, wherein the two tags or cylinders 34a and 34b are wrapped around the circumference of the femur and secured together by means of a medial knot 35, to thus provide a bonding seal between the open circumferential edge of the sealing device and the bone. Moreover, FIG. 4 shows the sealing device 30 in the form of a membrane stretched or tensioned over the bone aperture. The medullary cavity 19 and the underlying end of the femur shown in FIG. 2 are shaded and outlined at the proximal end of the membrane in FIG. 4.

FIG. 5 shows the next step, wherein a further sealing device 40, as for example described in WO 90/00375, U.S. Pat. No. 5,507,749, is put on the elastic membrane of the sealing device 30. The sealing device 40 consists of an elastic bottom portion 42 and a rigid top portion 44 usually having a circular upper edge 46. An inner bearing surface 48 within the top portion 44 of the sealing device 40 is formed in such a way that it has a positive fit with the front end of a bone cement cartridge; it has a shape corresponding to that of the tip of the cartridge (which is not shown) and is usually tapered to the bottom approximately in the form of a cone. The inner bearing surface 48 of the device 40, which is rotationally non-symmetrical, can be provided with an oval bottom outlet whose shape corresponds to the outlet of the cartridge. At the upper edge 46 of the top portion 44, two recesses 50 are provided with which pegs of the cartridge can engage in order to lock the cartridge in the sealing device 40 against rotation.

By means of the sealing device 30, first the opened end of the femur can be sealed, as described by means of FIGS. 3 and 4. Subsequently, before the bone cement is applied, the sealing device 40 is put thereonto, the membrane of the sealing device 30 is opened by a stab incision by means of a scalpel, the tip of the filled bone cement cartridge is pressed onto the inner bearing surface 48 of the sealing device 40 and the bone cement is applied in a way as for example described in WO 90/00375, U.S. Pat. No. 5,507, 749. By a combination according to the invention of the sealing device 40 with the membrane 30 according to the invention, it is possible to achieve an excellent and essentially vacuum-tight sealing of the opened end of the femur when applying bone cement, even if the bone surface of the opened proximal end of the femur is uneven or forms one or more angles.

What is claimed is:

1. A device for sealing an opening in a bone having a surface adjacent the opening comprising:

an elastic membrane positioned over the opening and vacuum sealed against the surface, the elastic membrane having a free edge; and a reinforcing layer on the free edge of the membrane to hold the free edge against the bone surface, the elastic membrane having a membrane opening therein aligned with the opening in the bone for introduction of material into the opening in the bone, the free edge of the membrane sealing against the bone when vacuum is applied on an opposite side of the opening in the bone from the membrane.

2. A device according to claim 1, wherein the elastic membrane is made of silicone.

3. A device according to claim 1, wherein the reinforced layer is a band around the free edge, and thickened portions in the reinforcing layer for urging the free edge of the elastic membrane against surface irregularities.

4. A device according to claim 1, wherein the reinforced layer is an elastic band positioned around the free edge to urge the free edge against the surface of the bone adjacent the opening.

5. A device according to claim 1, wherein the opening in the bone is in the end of a bone having a circumference, and the membrane has a shape that places the free edge around the bone against the circumference, the membrane having elongated tags extending therefrom on one side, and the tags being wrapped around the circumference of the bone and knotted together to provide the reinforcing layer forming a seal.

6. A device according to claim 1, wherein the bone has a circumference around the opening and the free edge of the elastic membrane is formed as an inflatable rim around the circumference and being inflated to form a circular seal around the bone.

7. A device according to claim 1, and a vacuum connection spaced from the opening in the bone for applying a vacuum to the opening in the bone.

8. A device according to claim 7, and a second sealing device inserted into the opening in the membrane and sealed relative thereto, said second sealing device being adapted to receiving a bone cement material for applying bone cement into the opening when the bone is under vacuum.

9. The method for introducing a material into an opening in a bone, comprising the steps of:

providing a membrane covering the opening and sealed against surfaces of the bone surrounding the opening;

providing a vacuum connection to the bone which opens to the opening in the bone;

providing a material to be introduced into the bone through the membrane into the opening in the bone when the opening is subjected to vacuum.

* * * * *